(12) United States Patent
Krutz et al.

(10) Patent No.: US 7,977,952 B2
(45) Date of Patent: Jul. 12, 2011

(54) POLYMERIC STRUCTURES AND METHODS FOR PRODUCING AND MONITORING POLYMERIC STRUCTURES

(76) Inventors: Gary Krutz, West Lafayette, IN (US); Keith Harmeyer, Batesville, IN (US); Michael Holland, Conrad, IA (US); Timu W. Gallien, Lafayette, IN (US)

( * ) Notice: Subject to any disclaimer, the term of this patent is extended or adjusted under 35 U.S.C. 154(b) by 257 days.

(21) Appl. No.: 12/341,215

(22) Filed: Dec. 22, 2008

(65) Prior Publication Data
US 2009/0189616 A1 Jul. 30, 2009

Related U.S. Application Data

(60) Provisional application No. 61/015,722, filed on Dec. 21, 2007.

(51) Int. Cl.
*G01R 31/12* (2006.01)
(52) U.S. Cl. ............... 324/548; 324/71.1; 73/866
(58) Field of Classification Search .............. 324/548, 324/71.1; 73/866, 114.77
See application file for complete search history.

(56) References Cited

U.S. PATENT DOCUMENTS

| | | | |
|---|---|---|---|
| 3,555,887 A | 1/1971 | Wood | |
| 4,399,100 A | 8/1983 | Zsolnay et al. | |
| 5,581,019 A * | 12/1996 | Minor et al. | 73/114.77 |
| 5,865,971 A | 2/1999 | Sunkara | |
| 5,966,018 A | 10/1999 | Edmunds et al. | |
| 6,498,496 B1 | 12/2002 | Keller et al. | |
| 6,958,615 B2 | 10/2005 | Poulbot et al. | |
| 7,009,409 B2 | 3/2006 | Davie et al. | |
| 2003/0164048 A1 | 9/2003 | Shkel | |
| 2005/0206096 A1 | 9/2005 | Browne et al. | |
| 2005/0268734 A1 * | 12/2005 | Watkins, Jr. et al. | 73/866 |
| 2006/0103081 A1 | 5/2006 | Dietrich et al. | |
| 2006/0196252 A1 | 9/2006 | Deckard | |
| 2007/0131035 A1 | 6/2007 | Krutz et al. | |

FOREIGN PATENT DOCUMENTS
JP H0976251 3/1997
* cited by examiner

*Primary Examiner* — Vincent Q Nguyen
(74) *Attorney, Agent, or Firm* — Hartman & Hartman, P.C.; Gary M. Hartman; Domenica N. S. Hartman

(57) ABSTRACT

A method for monitoring a component formed of a polymer material, and the polymer component. The component includes an electrically-conductive polymer sensing element integrally incorporated into the component. An electric potential is applied to the polymer sensing element, and an electric signal generated by the polymer sensing element is sensed in response to the polymer sensing element physically responding to a transitory or permanent distortion of the component. A signal can then be generated if the electric signal exceeds a predetermined threshold value for the component.

33 Claims, 4 Drawing Sheets

POLYMERIC STRUCTURES AND METHODS FOR PRODUCING AND MONITORING POLYMERIC STRUCTURES

CROSS REFERENCE TO RELATED APPLICATIONS

This application claims the benefit of U.S. Provisional Application No. 61/015,722, filed Dec. 21, 2007, the contents of which are incorporated herein by reference.

BACKGROUND OF THE INVENTION

The present invention generally relates to polymeric structures, and more particularly to methods and apparatuses for utilizing electrical properties of a polymer material to monitor a polymer component formed therefrom during the production and/or use of the component.

Polymer components, including seals and the like, are often critical to the performance of the products in which they are used. In such applications, catastrophic failure of the polymer component can be extremely detrimental to the product. Because of this, it is desirable to monitor reductions in performance and structural failures in polymer components. Because polymer components often have complex shapes or are installed in isolated locations, it can be difficult to monitor performance and structural failures with the use of conventional electronic sensors. In particular, the construction and materials for sensing elements of conventional electronic sensors are usually carefully selected to provide a highly responsive, repeatable and specific response to the property (or properties) of interest in order to provide suitable monitoring capabilities, yet the construction and material of a sensing element may not be well suited for use in combination with a polymer component. For example, if attempting to embed or integrate a sensing element into a polymer component, the material selected for the sensing element on the basis of its electrical properties may not be optimal in terms of structural, chemical or other physical properties required for compatibility with the polymer component.

Notwithstanding these challenges, methods and systems have been developed for the purpose of monitoring various polymer materials and structures. For example, U.S. Pat. No. 5,634,497 to Neto, U.S. Pat. No. 6,386,237 to Chevalier et al., and U.S. Pat. No. 6,498,991 to Phelan et al. disclose the detection of a worn hose by sensing the electrical resistivity in one or more wires embedded in the wall of the hose. These patents focus on detecting a discontinuity in the embedded wires, as would result from breakage of the wires due to wear as opposed to sensing a gradual increase in resistivity attributable to wear or deformation of the hose or its wires. U.S. Pat. No. 5,343,738 to Skaggs differs by disclosing a method for capacitively sensing the failure of a hose. In Skaggs, a fuel leakage through an inner layer of a hose is sensed on the basis of the leaked fuel altering the dielectric properties of an insulating material between a pair of copper wires embedded in the hose. Similar to Skaggs, U.S. Pat. No. 5,992,218 to Tryba et al. discloses sensing water leakage through a hose on the basis of the leaked water increasing the conductivity of an electrical insulating layer between a pair of conductor layers separated by the insulating layer. U.S. Pat. No. 5,969,618 to Redmond also discloses a method for detecting the failure of a hose on the basis of electrical conductivity. Redmond's hose is formed to have an annulus containing separated wires, and the failure of the inner layer of the hose is sensed when fluid leaks into the annulus and closes an electric circuit containing the wires.

Another approach to sensing an impending failure of a hose is disclosed in U.S. Pat. No. 4,446,892 to Maxwell. Maxwell discloses a fluid (oil) transport hose formed by at least two plies and a sensing element therebetween. In one embodiment of Maxwell, the sensing element is responsive to the electromagnetic properties of fluid present between the plies as a result of a failure of an inner ply of the hose. In a second embodiment of Maxwell, the sensing element is responsive to the failure of an inner ply of the hose by presenting an open circuit. The sensing element is said to preferably be a coil of fine wire wrapped around the inner ply and connected to means responsive to changes in the electrical impedance (AC) of the coil. Such changes are said to occur from fluid seepage into the material contacting with the coil or deformation of the inner ply, both of which change the inductance of the coil. In an alternative embodiment in which the sensing element is primarily intended to be responsive to the seepage of fluid (oil) between the plies of the hose, Maxwell employs parallel non-touching wires connected to means responsive to a change in conductance between the individual wires or to a change in the capacitance between the wires.

The prior art discussed above is particularly concerned with conduits through which a fluid is conveyed from one location to another, as opposed to fluid vessels such as hydraulic hoses, pipes, and tires in which little if any flow may occur and/or in which structural fatigue of a vessel wall from pressure cycles is often the most important factor in the life of the vessel. Furthermore, sensing systems of the type suggested by Maxwell are generally useful in relatively low pressure systems where the detection of seepage within the hose wall could provide an adequate warning of impending failure. However, in vessels subjected to fluids at relatively high pressures, once seepage occurs catastrophic failure is likely to occur in a matter of seconds, not hours or even minutes. Also, it is possible that a failure could occur in Maxwell's hose without detection as a result of occurring between wires, or a short could occur between wires that does not produce a significant signal.

U.S. Pat. No. 7,555,936 to Deckard addresses the shortcomings of the aforementioned prior art with a method and system capable of sensing and predicting fatigue failures of high-pressure vessel, such as hydraulic hoses or other types of pressurized conduits, as well as other structures subjected to high cyclical pressures. Deckard's system and method utilize a strain-sensing means disposed between an outermost layer of the vessel and an innermost layer of the vessel that is parallel to the outermost layer and contacts the fluid contained by the vessel. The strain-sensing means comprises at least one conductor parallel to the innermost layer of the wall. Changes are sensed in an electrical property associated with the conductor resulting from distortion of the wall of the vessel causing distortion of the at least one conductor. From such changes, a structural failure of the vessel can be predicted well in advance of the failure, allowing the vessel to be safely used for its full life and then replaced before any damage occurs to the fluid system containing the vessel and any objects surrounding the vessel.

U.S. Pat. No. 7,752,904 to Krutz et al. discloses structures having integral life-sensing capabilities as a result of the ability to monitor transitory and permanent distortions of the structures. Such a structure includes a pair of conductive layers and an intermediate layer therebetween formed of a dielectric, semiconductive, or resistive material, such that the conductive and intermediate layers form in combination an electrical element, namely, a capacitive or resistive element. The electrical element is located within the structure so as to be physically responsive to transitory and permanent distortions of the structure resulting from extrinsic and intrinsic sources. An electrical potential is applied to at least one of the conductive layers to generate an electrical signal from the electrical element. Transitory and/or permanent distortions of the structure are monitored by sensing changes in the electrical signal generated by the electrical element in response to the electrical element physically responding to the transitory and/or permanent distortion.

BRIEF DESCRIPTION OF THE INVENTION

The present invention provides for the use of conductive polymer materials to form at least part of a polymer component and serve as the primary sensing element of a sensing system capable of indicating significant signal changes prior to catastrophic failure of the component. The polymer sensing element is configured to be responsive to distortions within the component caused by extrinsic and intrinsic sources, such as the result of external forces applied to the structure and internal forces created as a result of wear, fatigue, and/or other structural breakdowns within the component that when sensed can detect an impending structural failure.

According to a first aspect of the invention, a method is provided for monitoring a component formed of a polymer material. The method includes forming the component to comprise an electrically-conductive polymer sensing element integrally incorporated into the component, applying an electric potential to the polymer sensing element, sensing an electric signal generated by the polymer sensing element in response to the polymer sensing element physically responding to a transitory or permanent distortion of the component, and generating a signal if the electric signal exceeds a predetermined threshold value for the component.

According to a second aspect of the invention, a polymer component is provided that includes an electrically-conductive polymer sensing element integrally incorporated into the component, and means for applying an electric potential to the polymer sensing element and generating an electric signal with the polymer sensing element in response to the polymer sensing element physically responding to a transitory or permanent distortion of the component.

Various sensing techniques can be utilized with the invention that are responsive to distortions and other physical conditions of a polymer component as sensed by the polymer sensing element. For example, the polymer sensing element can be used to monitor regular cyclic loading, as well as irregular loading or load distributions that occur from changing operating conditions or damage to the component. In this manner, the present invention provides the capability of continuously monitoring a polymer component and then repairing or removing the component from service before a catastrophic failure occurs.

According to another aspect of the invention, the sensing principals employed to monitor a polymer component can be used to monitor the curing of the polymer material used to form the component to ensure proper curing and detect process- and material-related defects. Such a method includes placing an uncured material mass between a pair of electrically-conductive plates, while heating the material mass, applying an electric potential across the plates to define a capacitive couple with the material mass, sensing a capacitive signal generated by the capacitive couple and discontinuing the curing process once the capacitive signal exceeds a predetermined threshold value for the curing process.

Other aspects and advantages of this invention will be better appreciated from the following detailed description.

DETAILED DESCRIPTION OF THE INVENTION

Figure 1:
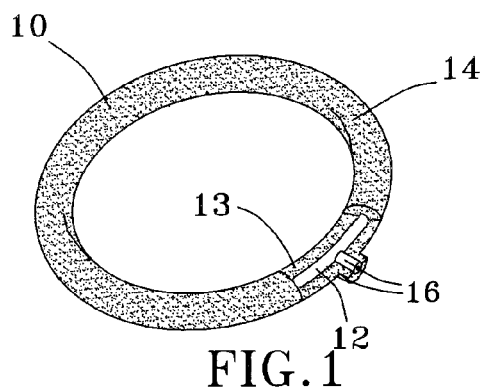
FIGS. 1 and 2 represent o-ring seals that can be formed of or formed to contain a polymer sensing element in accordance with embodiments of the invention.

The present invention involves the use of polymer materials that exhibit enhanced electrical properties, and the use of such properties to monitor the condition of a polymer component formed of or otherwise containing the polymer material. In effect, the polymer material defines a sensing element formed as an integral feature of the polymer component for the purpose of creating an electrical component capable of indicating the condition of the component. Polymer components within the scope of the invention include but are not limited to various types of seals (including o-ring seals and gaskets), as well as vibration isolators, fluid containers, belts, etc., that are often subject to transitory and permanent distortions leading to degradation of their performance. The output of the polymer sensing element is coupled to circuitry capable of indicating that a failure has or will soon occur. In some cases, the sensing element output can be coupled to data processing circuitry capable of predicting when a structural failure of the polymer component will occur in the future, so that the component can be safely used for its full life and then replaced before any damage occurs to the system containing the component or any surrounding structures.

Materials suitable for forming polymer sensing elements of this invention are capable of transmitting electric signals, yet retain physical properties that are superior to metals and other traditional conductor materials that are conventionally used to form sensing elements. Suitable polymer materials are also preferably capable of being fully embedded or otherwise integrated into the body of the polymer component to be monitored, necessitating that the polymer sensing element does not interfere with or degrade the desired properties of the polymer component. In so doing, the polymer sensing element is able to monitor the structural integrity, loading, and other measurable factors of the polymer component to provide useful information regarding the component.

Because a polymer sensing element of the invention is required to transfer an electric signal, at least part of the sensing element must be capable of at least measurable conductivity. For example, if the sensing element is part of a capacitive sensor, a conductive polymer material is used to form two conductive components separated by a dielectric. Measurable resistivity or conductivity is also required if the sensing element is part of a resistive or inductive sensor. To achieve an adequate level of conductivity in an otherwise dielectric polymer material (for example, about $4.4 \times 10^{16}$ ohm-cm for natural rubber and about $3.7 \times 10^{15}$ ohm-cm for styrene-butadiene rubber (SBR)), some type of conductive material must be added to the base polymer material of the sensing element. While the addition of metal filler can achieve an acceptable level of electrical conductivity, a preferred approach is to add conductive materials that, aside from electrical conductivity, will have little effect on the physical properties of the polymer material.

Figure 9:
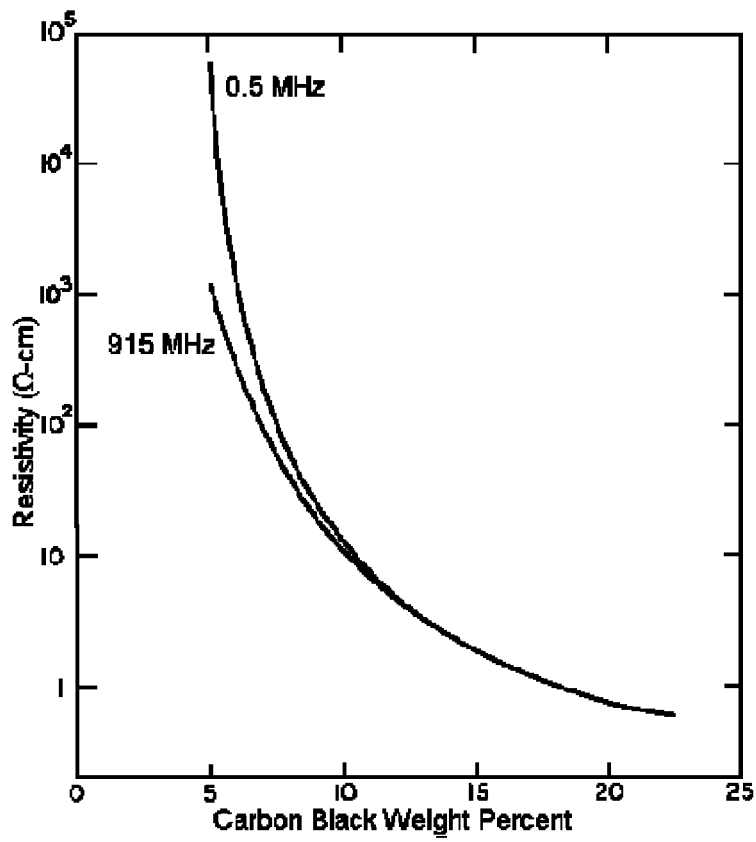
FIG. 9 is a graph plotting electrical resistivity of a polyvinyl chloride (PVC) polymer as a function of carbon black loading in the polymer.

While numerous fillers and extenders are known for use in compounding polymer and rubber materials, many have negligible effect on electrical conductivity. Examples of common rubber fillers and extenders include zinc oxide (ZnO), hydrated aluminum silicate and kaolinite mixtures (a commercial example of which is available under the name Dixie Clay® from R.T. Vanderbilt Co., Inc.), whiting (calcium carbonate), hydrous calcium magnesium silicate mineral mixtures (a commercial example of which is commercially available under the name Nytal®from R.T. Vanderbilt Co., Inc.), carbon black (a commercial example of which is commercially available under the name Thermax® from Cancarb, Ltd.), coumarone-indene resins (a commercial example of which is commercially available under the name Cumar®from the Neville Chemical Company, and mineral rubber (asphaltine minerals). Extenders such as coumarone-indene resins in SBR are known to contribute insulating characteristics by increasing volume resistivity. Conversely, carbon black (a form of amorphous carbon having a high surface area to volume ratio) has the capability of significantly lowering the resistivity of certain rubber materials when added at appropriate levels. Charge is believed to move through carbon polymer composites by way of tunneling of charge carriers, in which current flows as electrons travel through continuous carbon pathways and jump any gaps to get to the next pathway. On this basis, resistivity (and, inversely, conductivity) would be expected to be largely dependent on carbon black content. A nonlinear relationship between resistivity and carbon black content is evident from FIG. 9, which is a graph plotting electrical resistivity of a polyvinyl chloride (PVC) polymer as a function of carbon black loading in the polymer. Because carbon black generally does not adversely effect desirable properties of elastomers and polymers and in fact can promote certain properties if used in appropriate amounts, carbon black is believed to be a particularly suitable conductive filler material for use with the invention. Other potential additives that could be used include conductive salts. It is believed that a threshold of approximately 25% by volume of conductive filler (such as carbon black) typically must be reached before significant conductive properties are achieved, for example, resistivities of about 1 ohm-cm or less (corresponding to conductivities of about 0.1 (ohm-cm)$^{-1}$ or more).

FIGS. 1 through 8 represent various embodiments and applications for the use of polymer sensing elements of this invention. In these embodiments, annular-shaped seals are configured to utilize capacitance or resistivity to detect various strain and anomaly-related failure modes, for example, extrusion from a seal retaining gap, excessive squeeze, breakage or cracking, wear, stretching, twisting, and/or incorrect assembly. As the conductive polymer sensing elements of the seals strain under these failure modes, electrical properties of the sensing elements change. For example, the electrical capacitance or resistance of the sensing element can be continuously or intermittently measured or otherwise monitored to indicate the overall strain of the seal, as well as seal breakage. Relationships can be developed forgiven seal designs and materials that correlate electrical resistance to strain, as well as electrical resistance (or strain) to a model by which the remaining life of the seal can be predicted and a signal (digital, audio, visual, etc.) can be generated if the electrical resistance exceeds a predetermined threshold value for the seal. In this manner, the seals are able to indicate performance issues prior to catastrophic failure, and can be used in a wide variety of applications.

Figure 2:
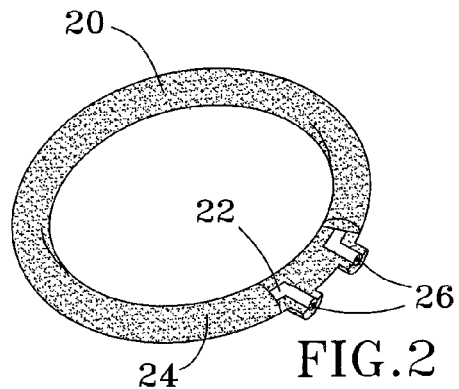

FIGS. 1 and 2 represent hydraulic elastomeric (o-ring) seals 10 and 20 configured to enable electrical measurements to be taken to monitor their operational status and alert an operator of an impending seal failure. The construction of the seal 10 in FIG. 1 is represented as including internal and external components 12 and 14, and an intermediate component 13. The internal and external components 12 and 14 are formed of conductive polymer materials, while the intermediate component 13 is formed of a dielectric material, preferably a nonconductive polymer material. The intermediate component 13 completely separates the internal and external components 12 and 14 to form a capacitor that serves as the polymer sensing element in accordance with an embodiment of the invention. A charge can be applied across the internal and external components 12 and 14 through a pair of contacts or leads 16 located on the outer periphery of the seal 10. Capacitance is monitored to indicate the presence of an anomaly that may lead to the failure of the seal 10. Application of the electric potential across the leads 16 can be continuous or intermittent, and changes in the output of the sensing element (capacitor 12-14) can be monitored and failure indicated by the output exceeding a predetermined threshold value for the output.

FIG. 2 shows the construction of the seal 20 as including internal and external components 22 and 24. The internal component 22 is preferably formed of a conductive polymer material to serve as a polymer sensing element in accordance with another embodiment of the invention. A charge can be applied to the internal component 22 through a pair of contacts or leads 26 located adjacent each other on the outer periphery of the seal 20, such that current effectively flows along the entire circumferential length of the seal 20. The current flow or resistance between the leads 26 of the internal component (sensing element) 22 is monitored to indicate the presence of an anomaly that may lead to the failure of the seal 20. As with the embodiment of FIG. 1, the application of the electric potential across the leads 26 can be continuous or intermittent, and changes in the output of the sensing element (component 22) can be monitored and failure indicated by the output exceeding a predetermined threshold value for the output.

Figure 3:
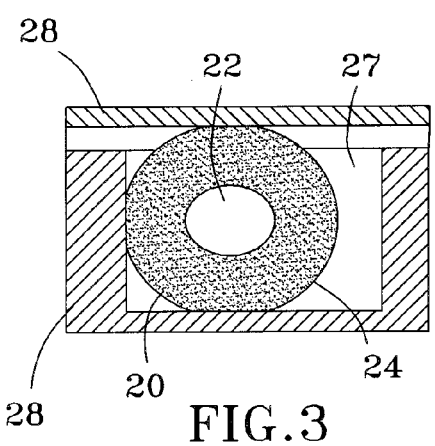
FIG. 3 is a cross-sectional representation of the o-ring seal of FIG. 2 disposed in an o-ring groove in the absence of pressure-induced distortion.
Figure 4:
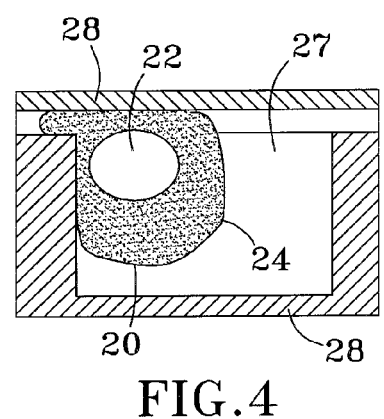
FIG. 4 is a cross-sectional representation of the o-ring seal subjected to conditions that distort the o-ring seal to the point of failure.

In FIGS. 3 and 4, the seal 20 of FIG. 2 is shown disposed in a groove 27 for providing fluidic sealing between two bodies 28. The deformation represented in FIG. 4 is illustrative of seal extrusion that would cause a significant change in one or more electrical properties (for example, resistivity) of the seal 20, and sufficient to cause the value of the electrical property to exceed a predetermined threshold value for the seal 20 based on previous baseline tests.

Figure 5:
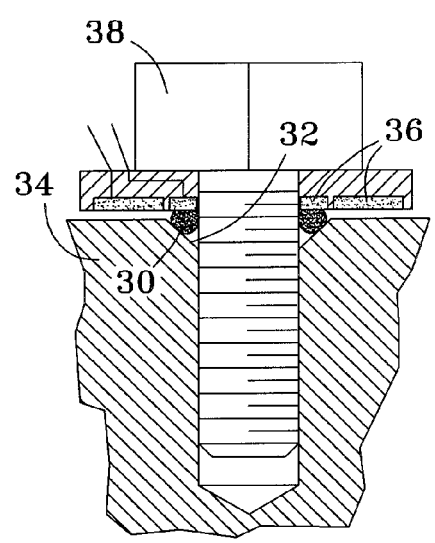
FIG. 5 is a cross-sectional representation of a bolt equipped with an o-ring seal in the absence of pressure-induced distortion.
Figure 6:
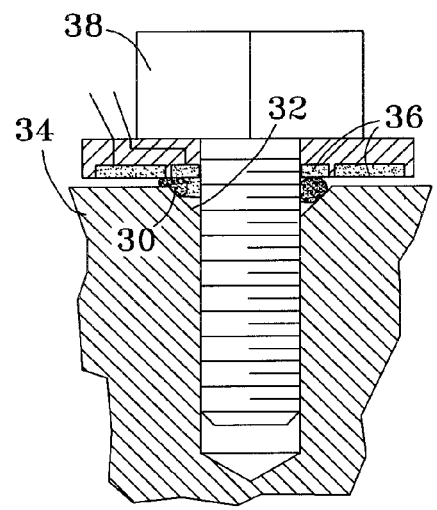
FIG. 6 is a cross-sectional representation of the bolt and o-ring seal of FIG. 3 subjected to conditions that distort the o-ring seal to the point of failure.

FIGS. 5 and 6 represent a seal 30 that may be constructed similar to that of FIGS. 3 and 4 but with the external component 24 formed of an electrically-conductive polymer, or with the entire seal 30 formed of a conductive polymer such that the entire seal 30 is effectively a polymer sensing element. The seal 30 is shown as used in combination with a bolt and washer assembly 38, with the seal 30 disposed in a chamfered recess 32 formed in a body 34 in which the assembly 38 is installed. The lower surface of the assembly 38 has two annular-shaped conductive rings 36, at least one of which is electrically charged. As seen in FIG. 5, the seal 30 contacts only one of the rings 36 under normal conditions, but when subjected to excess squeeze also contacts the other ring 36 to complete an electric circuit between the rings 36. The resistivity (or other suitable electric signal) of the electric circuit will depend in part on the extent of contact (surface area, pressure, etc.) between the seal 30 and rings 36, which can be compared to a predetermined threshold value that, if exceeded, indicates that the seal 30 has failed or will fail soon. In contrast to the prior embodiments, the rings 36 do not apply an electric potential to the seal 30 and the seal 30 does not generate an electric signal until the seal 30 has been sufficiently distorted to contact both rings 36. Furthermore, current does not flow along the circumferential length of the seal 30, but instead flows through the transverse width or thickness of the seal 30.

Figure 7:
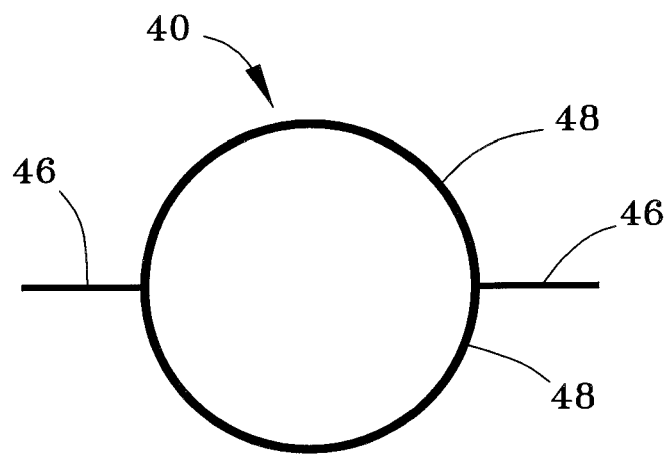
FIG. 7 is a plan view of an o-ring seal having two integrally-formed conductive leads.
Figure 8:
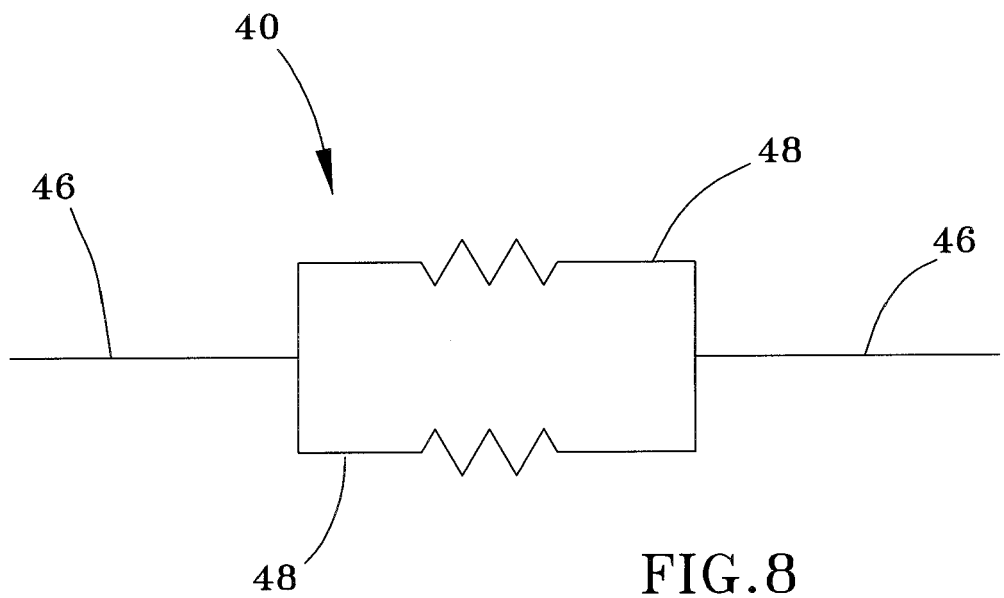
FIG. 8 is an electrical schematic that is representative of the o-ring seal of FIG. 7.

FIG. 7 represents a seal 40 similar to those of FIGS. 1 through 6, but modified to have two diametrically-opposed leads 46. By forming the entire seal 40 or an internal or external component (not shown) of a conductive polymer material, the resistance across the seal 40—from one lead 46 to the other 46—can be measured to monitor the performance of the seal 40. As represented in FIG. 8, the halves of the seal 40 between the leads 46 behave as two parallel resistors, and excessive strain in either half 48 will result in a change in the electrical resistance measured at the leads 46.

Figure 10:
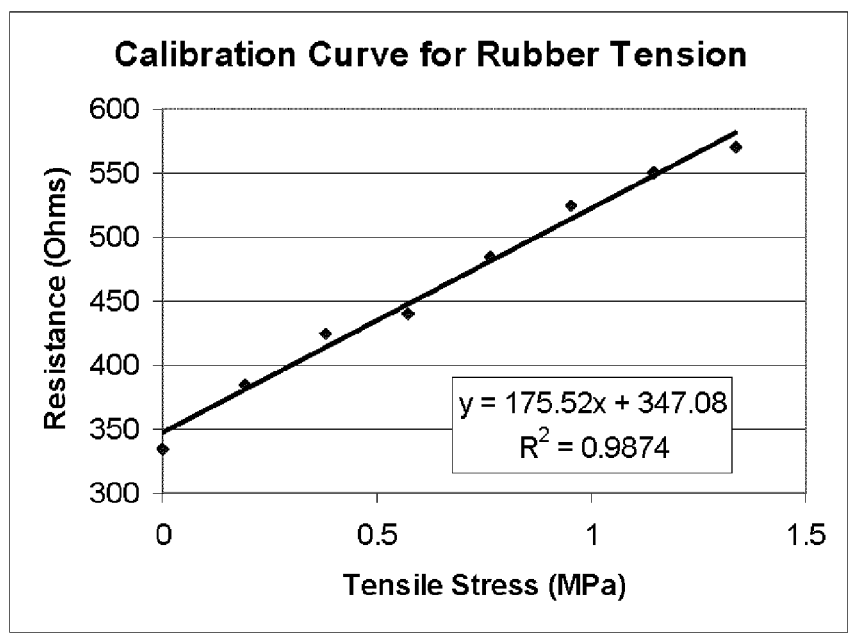
FIG. 10 is a graph plotting data obtained from a sensitivity test conducted with a semi-conductive rubber compound.

The capabilities of polymer sensing elements of the type described above have been investigated. A series of preliminary tests were conducted to validate the sensitivity of polymer sensing elements and to determine the ability of conductive polymers to make LCR (inductance, capacitance or resistance) sensing elements. The polymer utilized in a first experiment was a rubber compound commercially available from GE Silicones under the name SE877 TUFEL®. This polymer is a black semiconductive silicone rubber compound that is sufficiently conductive for use to discharge static electricity. The sample was formed into a long strip about 50 mm wide and about 1 mm thick, and cured according to specifications for the material. A Hewlett Packard 3435A multimeter was used to perform resistance measurements. A 50 mm length strip of the sample was used to perform a calibration curve. The strip was clamped on both ends and gradually placed under tension. The force on the strip was measured with a spring scale accurate to about 0.5 N (0.11 lb). FIG. 10 is a plot of the results up to about tensile load of 200 psi (about 1.38 MPa), at which point the strip broke. A regression line is shown fit to the data to determine the slope of the curve, which corresponds to the sensitivity of the polymer material. The results evidence a sensitivity of about 175.5 ohms/MPa (about 1.21 ohms/psi).

Figure 11:
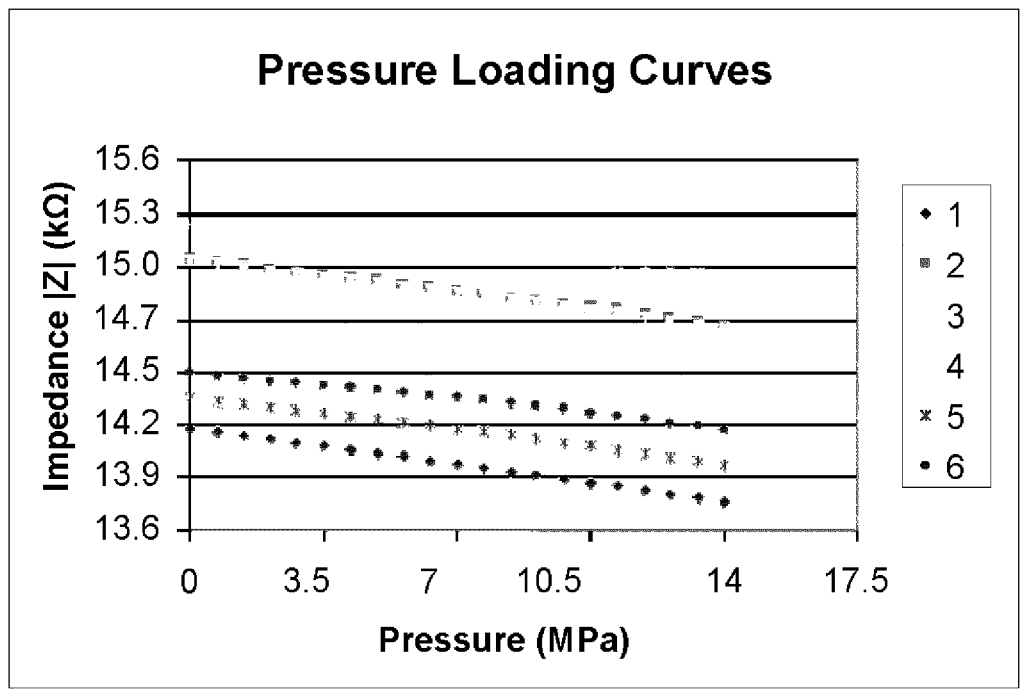
FIG. 11 is a graph representing pressure loading curves obtained with six specimens of a conductive polymer material.

Testing was also performed on samples of a proprietary conductive polymer utilizing LCR measurements (at 10 kHz) to monitor changes in structure that would be critical to performance and lead to cracking or breaking of the material. FIG. 11 is a graph representing pressure loading curves obtained with six specimens of the conductive polymer and indicates a consistent correlation between impedance and pressure, as evidenced by the approximately equal slopes of the curves. As evident from FIG. 11, the specimens exhibited an impedance of about 14 to about 15 kilo-ohms without any load. Differences in the absolute measurement values of the samples were attributed to slight structural differences.

Figure 12:
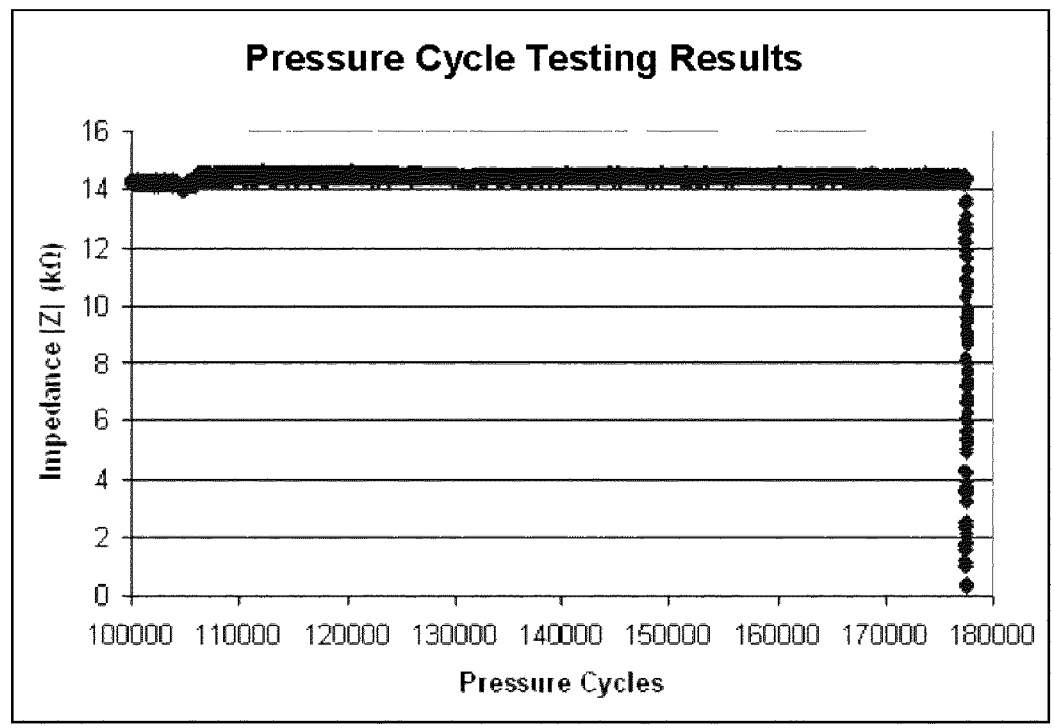
FIG. 12 is a graph plotting pressure cycle test results obtained with a specimen formed of a conductive polymer material.

To test the functionality of a polymer sensing element under cyclic conditions, fatigue tests were performed on the six specimens evaluated in the prior test. The results of the fatigue test for one of the specimens are plotted in FIG. 12, which indicates that the measured impedance value is roughly equal to the impedance values plotted in FIG. 11. Approximately one hundred cycles before a catastrophic failure occurred (at cycle 177503), the impedance measurement suddenly dropped to about one and fluctuated around this level until approximately twenty-five cycles before failure, at which point the impedance became nearly constant until catastrophic failure occurred. With the exception of the fourth specimen, the results of the remaining five specimens were similar. The fourth specimen contained an apparent assembly error that resulted in its measured impedance being low even before the load was applied. Of the five valid specimens, each exhibited a drastic drop in impedance prior to failure. Specifically, specimens #1, #2, #3, #5, and #6 exhibited drops in impedance of, respectively, about 95%, about 93%, about 75%, about 91%, and about 99% at, respectively, 526, 101, 195, 313 and 561 cycles prior to failure. These results evidenced that an impending catastrophic fatigue failure could be predicted well in advance of an actual failure.

From the foregoing, it was concluded that polymer sensing elements are capable of electrical measurements that can be used to monitor the condition of a polymer component, which may be formed by the sensing element or in which the sensing element is embedded. Furthermore, the tests described above evidenced that polymer sensing elements can adequately and consistently predict changes in structure of the type that may lead to catastrophic failure. In view of the fatigue test results, it was also concluded that polymer sensing elements are capable of sensitivity limits that are sufficiently high to avoid erroneous signals of impending failure.

Figure 13:
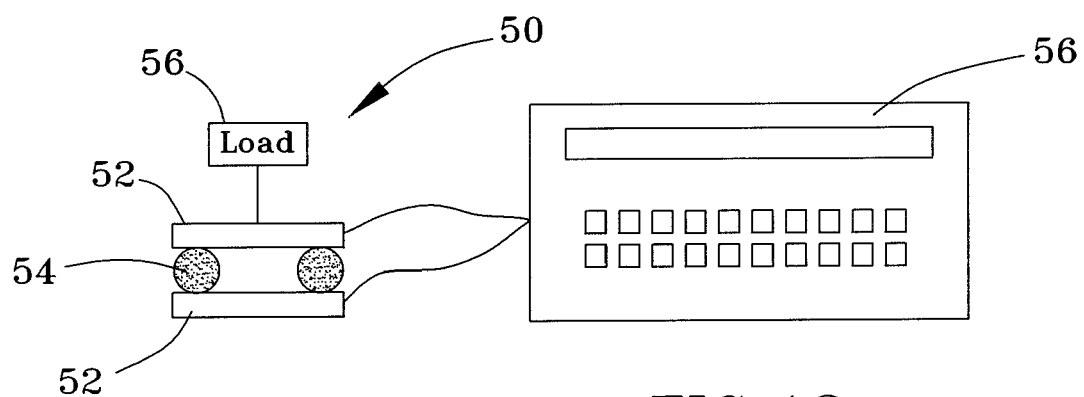
FIG. 13 schematically represents a polymer cure monitoring system in accordance with another embodiment of the invention.

The invention also encompasses the further use of electrical properties of polymers to evidence their vulcanization state during cure. This aspect of the invention is schematically represented in FIG. 13, which depicts a polymer cure monitoring system 50 in accordance with an embodiment of the invention. The system 50 comprises a pair of conductive (e.g., metal) plates 52 separated by and contacting an uncured mass 54 (represented as an o-ring seal) undergoing cure according to the particular time-temperature conditions for the polymer composition of the mass 54. A load 56 is applied to ensure constant and uniform contact between the plates 52 and the mass 54, which effectively form a capacitor whose capacitance value will depend on the size, shape and dielectric constant of the mass 54, the size and distance between the plates 52, and an electric charge applied to the plates 52. According to this aspect of the invention, for a particular type of polymer and shape and size of the mass 54, capacitance readings taken across the plates 52 with a suitable LCR meter 56 (or other suitable device) will change as the mass 54 cures. By performing baseline tests to establish a curve comparing cure state to capacitance value, a threshold value can be established for the particular mass 54 by which the cure state of subsequent masses of essentially the same size, shape and material can be estimated. The curing process for a given mass 54 can then be discontinued once the capacitive value reaches or exceeds the predetermined threshold value established for its particular curing process. Such a process can be used to monitor cure processes for a variety of polymeric materials, including elastomers and particularly articles formed of rubber materials such as tires, o-ring seals, gaskets, etc. The process has the advantages of a convenient and low-cost nondestructive examination (NDE) that can be performed in-line during the manufacture of production materials in their final form.

While the invention has been described in terms of specific embodiments, it is apparent that other forms could be adopted by one skilled in the art. For example, the physical configuration of the polymer component could differ from that shown, and materials and processes other than those noted could be use. Therefore, the scope of the invention is to be limited only by the following claims.

The invention claimed is:

1. A method of monitoring a component formed of a polymer material, the method comprising:
    forming the component to comprise a dielectric polymer portion and at least one electrically-conductive polymer sensing element integrally incorporated as a discrete feature of the component;
    applying a force to the component that at least transitorily distorts at least an external surface portion of the component;
    applying an electric potential to the polymer sensing element;
    sensing an electric signal generated by the polymer sensing element in response to the polymer sensing element physically responding to distortion of the component caused at least in part by the force; and
    generating a signal if the electric signal exceeds a predetermined threshold value for the component.

2. The method according to claim 1, wherein the polymer sensing element is one of two conductors of a capacitor and the electric signal is a capacitance of the capacitor.

3. The method according to claim 1, wherein the polymer sensing element has a resistivity of about 1 ohm-cm or less.

4. The method according to claim 1, wherein the polymer sensing element is entirely embedded within the component.

5. The method according to claim 1, wherein the polymer sensing element defines the external surface portion of the component.

6. The method according to claim 1, wherein the application of the electric potential to the polymer sensing element causes the polymer sensing element to generate the electric signal, and the sensing step comprises sensing changes in the electric signal resulting from the polymer sensing element physically responding to the distortion of the component.

7. The method according to claim 1, wherein the electric potential is not applied to the polymer sensing element and the polymer sensing element does not generate the electric signal until distortion of the polymer sensing element has occurred as a result of the polymer sensing element physically responding to the distortion of the component.

8. The method according to claim 7, wherein the application of the electric potential to the polymer sensing element is caused by the distortion of the component causing the polymer sensing element to contact a pair of leads across which the electrical potential exists.

9. The method according to claim 1, wherein the electric signal is generated by a current that enters and exits the component at leads adjacent to each other on the component.

10. The method according to claim 1, wherein the electric signal is generated by a current that flows through a transverse width of the component.

11. The method according to claim 1, wherein the electric signal is generated by a current that enters and exits the component at leads at opposite ends of the component.

12. The method according to claim 1, wherein the component is a seal.

13. The method according to claim 12, wherein the seal has an annular shape.

14. The method according to claim 12, wherein the seal is disposed in a groove and the predetermined threshold value of the electric signal corresponds to extrusion of the seal.

15. The method according to claim 12, wherein the seal is disposed around in a bolt assembly and the electric signal is generated by the polymer sensing element in response to excess squeeze of the seal.

16. The method according to claim 1, wherein the component is formed of an elastomer.

17. A polymer component comprising:
    a dielectric polymer portion;
    at least one electrically-conductive polymer sensing element integrally incorporated as a discrete feature of the component and adapted to physically respond to a distortion of the component caused by a force applied to the component that at least transitorily distorts at least an external surface portion of the component;
    means for applying an electric potential to the polymer sensing element and generating an electric signal with the polymer sensing element in response to the polymer sensing element physically responding to the distortion of the component caused at least in part by the force applied to the component.

18. The polymer component according to claim 17, further comprising means for generating a signal if the electric signal exceeds a predetermined threshold value for the component.

19. The polymer component according to claim 17, wherein the polymer sensing element is one of two conductors of a capacitor and the electric signal is a capacitance of the capacitor.

20. The polymer component according to claim 17, wherein the polymer sensing element has a resistivity of about 1 ohm-cm or less.

21. The polymer component according to claim 17, wherein the polymer sensing element is entirely embedded within the polymer component.

22. The polymer component according to claim 17, wherein the polymer sensing element defines the external surface portion of the component.

23. The polymer component according to claim 17, wherein the applying means does not apply the electric potential to the polymer sensing element and the polymer sensing element does not generate the electric signal until distortion of the polymer sensing element has occurred as a result of the polymer sensing element physically responding to the distortion of the polymer component.

24. The polymer component according to claim 23, wherein the polymer component is part of an assembly comprising a pair of leads across which the electrical potential exists and the polymer sensing element contacts if the component is distorted.

25. The polymer component according to claim 17, wherein the polymer component is configured so that electrical current enters and exits the polymer component at leads adjacent to each other on the polymer component.

26. The polymer component according to claim 17, wherein the polymer component is configured so that electrical current flows through a transverse width of the polymer component.

27. The polymer component according to claim 17, wherein the polymer component comprises leads at opposite ends thereof.

28. The polymer component according to claim 17, wherein the polymer component is a seal.

29. The polymer component according to claim 28, wherein the seal has an annular shape.

30. The polymer component according to claim 28, wherein the seal is disposed in a groove and the distortion of the component is extrusion of the seal.

31. The polymer component according to claim 28, wherein the seal is disposed around in a bolt assembly and the electric signal is generated by the polymer sensing element in response to excess squeeze of the seal.

32. The polymer component according to claim 17, wherein the polymer component is formed of an elastomer.

33. A method of monitoring a curing process of a polymer material, the method comprising:
- placing an uncured material mass between a pair of electrically-conductive plates;
- while heating the material mass, applying an electric potential across the plates to define a capacitive couple with the material mass;
- sensing a capacitive signal generated by the capacitive couple; and
- discontinuing the curing process once the capacitive signal exceeds a predetermined threshold value for the curing process.

* * * * *